United States Patent
Sugumi et al.

(10) Patent No.: US 11,321,042 B2
(45) Date of Patent: May 3, 2022

(54) DISPLAY SYSTEM AND PROGRAM

(71) Applicant: EIZO Corporation, Hakusan (JP)

(72) Inventors: Masahiro Sugumi, Hakusan (JP); Airi Kurokawa, Hakusan (JP); Hideaki Hashimoto, Hakusan (JP); Tatsuya Nakamura, Hakusan (JP); Wei Song, Hakusan (JP)

(73) Assignee: EIZO Corporation, Hakusan (JP)

( * ) Notice: Subject to any disclaimer, the term of this patent is extended or adjusted under 35 U.S.C. 154(b) by 8 days.

(21) Appl. No.: 16/980,942

(22) PCT Filed: Mar. 19, 2019

(86) PCT No.: PCT/JP2019/011312
§ 371 (c)(1),
(2) Date: Sep. 15, 2020

(87) PCT Pub. No.: WO2019/188532
PCT Pub. Date: Oct. 3, 2019

(65) Prior Publication Data
US 2020/0409646 A1 Dec. 31, 2020

(30) Foreign Application Priority Data
Mar. 28, 2018 (JP) .............................. JP2018-062235

(51) Int. Cl.
*G06F 3/14* (2006.01)
*G16H 10/60* (2018.01)
(Continued)

(52) U.S. Cl.
CPC .......... *G06F 3/1446* (2013.01); *G06F 3/1423* (2013.01); *G06F 3/1431* (2013.01);
(Continued)

(58) Field of Classification Search
CPC .... G06F 3/1446; G06F 3/1431; G06F 3/1438; G06F 3/1454; G06F 3/1423; G06F 9/452;
(Continued)

(56) References Cited

U.S. PATENT DOCUMENTS 5,900,863 A   5/1999  Numazaki
7,984,108 B2 * 7/2011  Landis ................ G06F 11/1474
                                                 709/215
(Continued)

FOREIGN PATENT DOCUMENTS

CN   103677992 A   3/2014
JP   S62-288924 A  12/1987
(Continued)

OTHER PUBLICATIONS

English Translation of Prior Art WO2014181420 provided in IDS on May 10, 2021. (Year: 2014).*
(Continued)

Primary Examiner — Vijay Shankar
(74) Attorney, Agent, or Firm — Maier & Maier, PLLC

(57) ABSTRACT

The present invention provides a display system comprising: first and second information processing devices; first and second display devices configured to switch between a first display mode, in which a first image output from the first information processing device is displayed across the first and second display devices, and a second display mode, in which a second image output from the second information processing device is displayed across the first and second display devices; a detector configured to detect whether a pointing position is positioned on a switch area arranged in at least one of the first and second display devices; and a display switcher configured to, when the detector detects the
(Continued)

pointing position on the switch area in the first display mode, switch a display mode from the first display mode to the second display mode.

5 Claims, 14 Drawing Sheets

(51) Int. Cl.
*G16H 30/40* (2018.01)
*G09G 5/14* (2006.01)

(52) U.S. Cl.
CPC ............ *G06F 3/1438* (2013.01); *G09G 5/14* (2013.01); *G16H 10/60* (2018.01); *G16H 30/40* (2018.01); *G09G 2300/026* (2013.01); *G09G 2370/20* (2013.01); *G09G 2380/08* (2013.01)

(58) Field of Classification Search
CPC .. G06F 3/0482; G06F 3/0488; G06F 3/04883; G09G 5/14; G09G 2300/026; G09G 2370/20; G09G 2380/08; G09G 5/08; G09G 2354/00; G09G 5/00; G16H 10/60; G16H 30/40; G16H 10/00; A61B 5/0002; A61B 5/7445
See application file for complete search history.

(56) References Cited

U.S. PATENT DOCUMENTS

| | | | | |
|---|---|---|---|---|
| 8,094,647 B2* | 1/2012 | Elliott | ................ | H04L 29/06 |
| | | | | 370/352 |
| 9,189,018 B2* | 11/2015 | Sirpal | ................ | H04M 1/0256 |
| 10,607,571 B2* | 3/2020 | Utsch | ................ | G06F 3/1446 |
| 11,099,801 B2* | 8/2021 | Sugumi | ................ | G06F 3/1423 |
| 2009/0028402 A1 | 1/2009 | Ando | | |
| 2010/0045594 A1 | 2/2010 | Jenks et al. | | |
| 2010/0123732 A1 | 5/2010 | Jenks et al. | | |
| 2010/0180055 A1 | 7/2010 | Lyon et al. | | |
| 2012/0249398 A1* | 10/2012 | Kanda | ................ | G06F 3/1423 |
| | | | | 345/4 |
| 2014/0098006 A1 | 4/2014 | Jenks et al. | | |
| 2020/0264908 A1* | 8/2020 | Utsch | ................ | H04L 65/608 |

FOREIGN PATENT DOCUMENTS

| | | |
|---|---|---|
| JP | H09-091079 A | 4/1997 |
| JP | H10-214070 A | 8/1998 |
| JP | 2002-189542 A | 7/2002 |
| JP | 2003-210414 A | 7/2003 |
| JP | 2004-70635 A | 3/2004 |
| JP | 2008-040190 A | 2/2008 |
| JP | 2008-090640 A | 4/2008 |
| JP | 2011-107914 A | 6/2011 |
| JP | 2018-41024 A | 3/2018 |
| WO | 2007/099816 A1 | 9/2007 |
| WO | 2014181420 A1 | 11/2014 |

OTHER PUBLICATIONS

International Search Report dated Jun. 18, 2019 in corresponding International application No. PCT/JP2019/011312; 4 pages.
[Online], Jun. 6, 2007, [retrieval date Jan. 22, 2019]Internet: <URL:https://oshiete.goo.ne.jp/qa/3049256.html>, non-official translation ("I would like to use 2 PCs with dual display . . . , Oshiete! goo"); 9 pages.
Japanese Office Action dated Sep. 18, 2018 in corresponding Japanese application No. 2018-062235; 6 pages.
Japanese Office Action dated Feb. 19, 2019 in corresponding Japanese application No. 2018-062235; 6 pages.
Japanese Office Action dated Jun. 11, 2019 in corresponding Japanese application No. 2018-062235; 8 pages.
Extended European Search Report dated Apr. 7, 2021, in connection with corresponding EP Application No. 19775296.7; 10 pages.

* cited by examiner

DISPLAY SYSTEM AND PROGRAM

TECHNICAL FIELD

The present invention relates to a display system that combines multiple display devices and multiple Information processing devices.

BACKGROUND ART

There is known a display system in which a plurality of information processing devices are connected to a display device and images are displayed on the display device. For example, in a hospital, a plurality of information processing devices are respectively connected to a plurality of display devices, and the image displayed on the display devices is switched from the image of one information processing device to the image of another information processing device according to situations. For example, in a case that one information processing device is configured to connect to the server of hospital X and another information processing device is configured to connect to the server of hospital Y, the doctors switch the image displayed on the display device from the image of the one information processing device to the image of another information processing device to compare the images stored in the servers of hospitals X and Y.

Patent literature 1 discloses a workstation switching device configured to switch the image displayed on the display device among the images of workstations by only operating a mouse in addition to operating a mechanical switch and a keyboard.

CITATION LIST

Patent Literature

[Patent Literature 1] Japanese Unexamined Patent Application Publication No. 2002-189542

SUMMARY OF INVENTION

Problems to be Solved by the Invention

The present invention provides a display system, in which a plurality of information processing devices are connected to a display device and each of the information processing devices can display an image on the display device, can suitably switch the image displayed on the display device.

Solution to Problem

Various embodiments of the present invention are illustrated below. The embodiments shown below can be combined.

The present invention provides a display system comprising: first and second information processing devices; first and second display devices configured to switch between a first display mode, in which a first image output from the first information processing device is displayed across the first and second display devices, and a second display mode, in which a second image output from the second information processing device is displayed across the first and second display devices; a detector configured to detect whether a pointing position is positioned on a switch area arranged in at least one of the first and second display devices; and a display switcher configured to, when the detector detects the pointing position on the switch area in the first display mode, switch a display mode from the first display mode to the second display mode.

The present invention provides the display system comprises the first and second information processing devices, and the first and second display devices. The first and second display devices are configured to switch between the first and second display modes. In the first display mode, the first image output from the first information processing device is displayed across the first and second display devices. In the second display mode, the second image output from the second information processing device is displayed across the first and second display devices. And the display system comprises the detector configured to detect whether the pointing position is positioned on the switch area arranged in at least one of the first and second display devices, and the display switcher configured to, when the detector detects the pointing position on the switch area in the first display mode, switch a display mode from the first display mode to the second display mode. Thus, the display system can easily switch the image displayed across the first and second display devices between the first and second images by moving the pointing position to the switch area.

Various embodiments of the present invention are illustrated below. The embodiments shown below can be combined.

Preferably, the first and second display devices each include an end portion provided in a direction perpendicular to a direction in which the first and second display devices are arranged, the switch area is arranged in the end portion of the first display device or the end portion of the second display device.

Preferably, the switch area includes at least one of a first switch area arranged in the first display device and a second switch area arranged in the second display device, the display switcher, when the detector detects the pointing position on the first switch area, switches the display mode from the first display mode to the second display mode.

Preferably, the switch area includes at least one of a first switch area arranged in the first display device and a second switch area arranged in the second display device, the display switcher, when the detector detects the pointing position on the first switch area, switches the display mode from the second display mode to the first display mode.

Preferably, the display switcher displays information, indicating whether an image displayed on the first and second display devices is the first image or the second image, on at least one of the first and second display devices.

Preferably, the first display device or the second display device is configured to display an electrical health record.

Another aspect of the present embodiments provides a program causing a computer to function as a controller that controls a display system including first and second information processing devices and first and second display devices, the first and second display devices being configured to switch between a first display mode, in which a first image output from the first information processing device is displayed across the first and second display devices, and a second display mode, in which a second image output from the second information processing device is displayed across the first and second display devices, the program comprising: detecting, by a detector, whether a pointing position is positioned on a switch area arranged in at least one of the first and second display devices; and switching, by a display switcher, a display mode from the first display mode to the second display mode when the detector detects the pointing position on the switch area in the first display mode.

DESCRIPTION OF EMBODIMENTS

Hereinafter, the embodiments of the present invention will be described with reference to the drawings. The various features shown in the embodiments below can be combined.

1. First Embodiment 1-1. Display System 10

Figure 1:
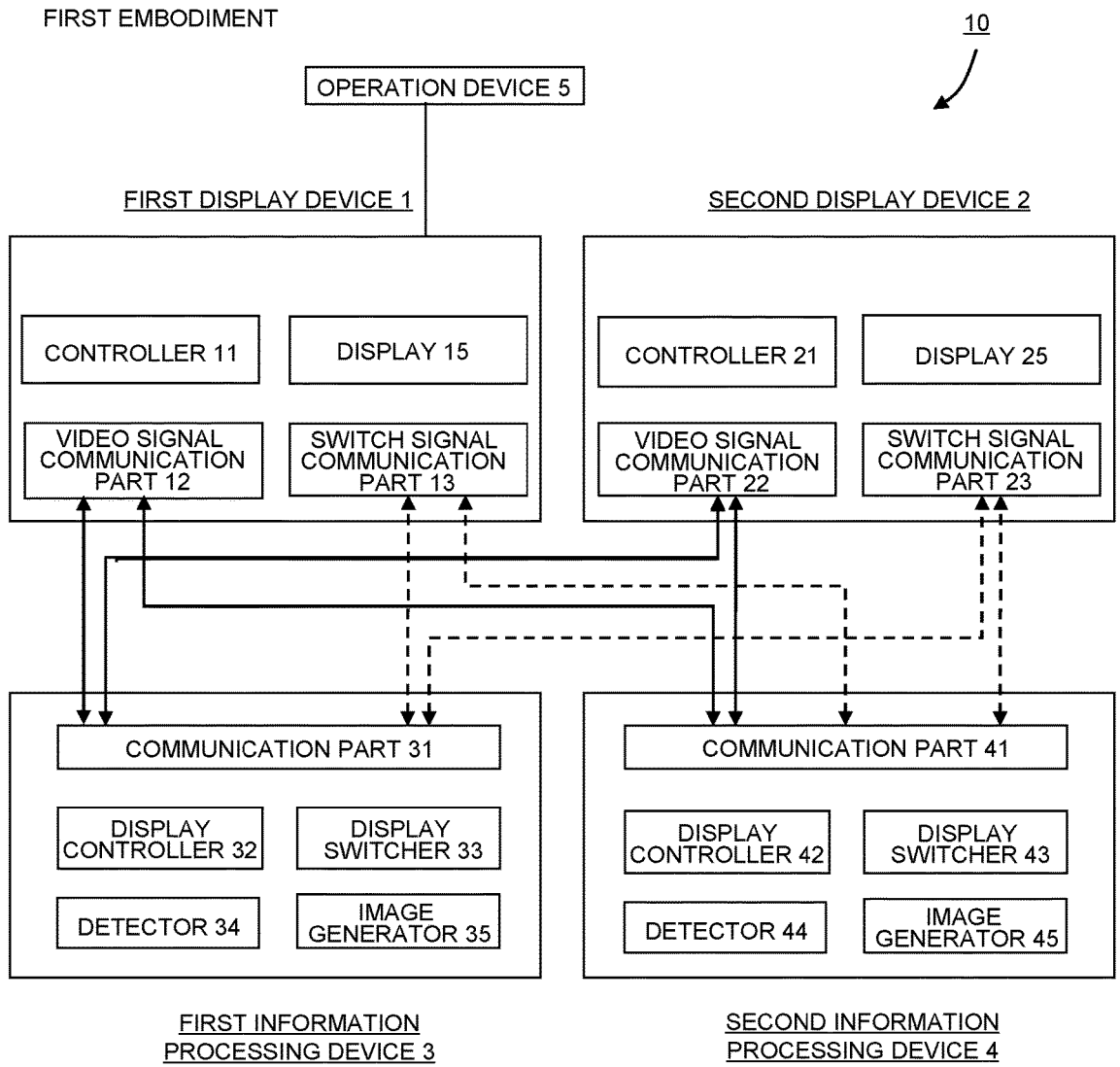
FIG. 1 is a functional block diagram showing a configuration of a display system 10 according to the first embodiment of the present invention.

The display system 10, according to the first embodiment of the present invention, will be described with reference to FIG. 1. As shown in FIG. 1, the display system 10 includes first and second information processing devices 3 and 4, and first and second display devices 1 and 2.

The first and second display devices 1 and 2 are configured to switch display mode between a first and second display mode. In the first display mode, the first image, which is the image output from the first information processing device 3, is displayed across the first and second display devices 1 and 2. That is, the first and second display devices 1 and 2 perform extended display with respect to the first image. In the second display mode, the second image, which is the image output from the second information processing device 4, is displayed across the first and second display devices 1 and 2. That is, the first and second display devices 1 and 2 perform extended display with respect to the second image. The display system 10 includes detectors 34 and 44 that detect whether the pointing position PP is positioned on a switch area arranged in at least one of the first and second display devices 1 and 2. And the display system 10 includes display switchers 33 and 43 that switch, when detector 34 detects the pointing position PP in the first display mode, the display mode from the first display mode to the second display mode. The details will be described below.

<First Information Processing Device 3>

The first information processing device 3 includes a communication part 31, a display controller 32, a display switcher 33, a detector 34, and an image generator 35.

The communication part 31 communicates various signals with the first and second display devices 1 and 2. The image generator 35 generates various image data. In this embodiment, image data generated by the first information processing device 3 is defined as a first image, and image data generated by the second information processing device 4 is defined as a second image. Here, the image data includes data corresponding to a still image and a moving image. The display controller 32 is configured to display the image generated by the image generator 35 on the first and second display devices 1 and 2. The display switcher 33 switches the image displayed on the first and second display devices 1 and 2. In this embodiment, the display switcher 33 generates a switch signal for switching the image, which is displayed on the first and second display devices 1 and 2, from the first image to the second image. The detector 34 is configured to detect whether the pointing position PP is positioned on the switch area arranged in at least one of the first and second display devices 1 and 2. In the present embodiment, the first and second display devices 1 and 2 each includes an end portion in a direction perpendicular to a direction in which the first and second display devices 1 and 2 are arranged, and the switch area SR is arranged in at least one of the ends of the first and second display devices 1 and 2. Details of the detector 34 will be described later. In the present embodiment, the display switcher 33 is configured to, when detector 34 detects the pointing position PP in the first display mode, switch the display mode from the first display mode to the second display mode.

<Second Information Processing Device 4>

The second information processing device 4 includes a communication part 41, a display controller 42, a display switcher 43, the detector 44, and an image generator 45. Since the functions of the communication part 41, the display controller 42, the display switcher 43, the detector 44 and the image generator 45 are the same as the communication part 31, the display controller 32, the display switcher 33, the detector 34, and the image generator 35 of the first information processing device 3, and thus details of the functions are omitted.

<First Display Device 1>

The first display device 1 includes a controller 11, a video signal communication part 12, a switch signal communication part 13, and a display 15.

The controller 11, which corresponds to CPU, for example, reads a program stored in a memory (not shown) and executes various arithmetic processing. The video signal communication part 12 is configured to communicate a video signal with between the first and second information processing devices 3 and 4. Here, the video signal is an electric signal of an image and is used for communications of image data. In the present embodiment, the video signal communication part 12 is configured to communicate with the communication part 31 of the first information processing device 3 and the communication part 41 of the second information processing device 4. The switch signal communication part 13 communicates various switch signals between the first and second information processing devices 3 and 4. In the present embodiment, the switch signal communication part 13 is configured to communicate with the communication part 31 of the first information processing device 3 and the communication part 41 of the second information processing device 4. Further, the switch signal is transmitted and received between the first display device 1 and the processing devices of the first and second information processing devices 3 and 4 through the switch signal communication part 13.

The video signal communication part 12 and the switch signal communication part 13 are connected to the communication part 31 by wire or wireless.

The display 15 is configured to display input image data as the image, and the display 15 corresponds to, for example, a liquid crystal display, an organic EL display, a touch panel display, and an electronic paper.

Further, an operation device 5 is connected to the first display device 1. In this embodiment, the operation device 5 is configured to operate one of the first and second information processing devices 3 and 4 that outputs the image to the first and second display devices 1 and 2. Specifically, when the image displayed on the first display device 1 and the second display device 2 in the extended display manner is the first image, the operation device 5 is capable of operating the first information processing device 3. And when the image displayed on the first and second display devices 1 and 2 in the extended display manner is the second image, the operation device 5 is capable of operating the second information processing device 4. Besides, the operation device 5 is configured to indicate the pointing position PP (see FIG. 3) on the first and second display devices 1 and 2.

<Second Display Device 2>

The second display device 2 includes a controller 21, a video signal communication part 22, a switch signal communication part 23, and a display 25. The functions of the controller 21, the video signal communication part 22, the switch signal communication part 23, and the display 25 are the same as those of the controller 11, the video signal communication part 12, the switch signal communication part 13, and the display 15, and thus details of the functions are omitted.

Each of the above components may be realized by software or hardware. When realized by software, various functions can be realized by the CPU executing programs. The program may be stored in built-in memory or a non-transitory readable medium by a computer. Alternatively, the above functions are realized by reading the program stored in external memory using so-called cloud computing. When realized by hardware, the above functions can be performed by various circuits such as ASIC, FPGA, or DRP. The present embodiment deals with various information and concepts including this information, and the various information is a bit group of binary numbers having 0 or 1, and the various information is represented according to the level of signal value. And in the present embodiment, communications and calculations can be executed according to configurations of the above software and hardware.

1-2. Flowchart of First Embodiment

Next, the processing executed by the display system 10 will be described with reference to FIGS. 2 to 6.

Figure 3:
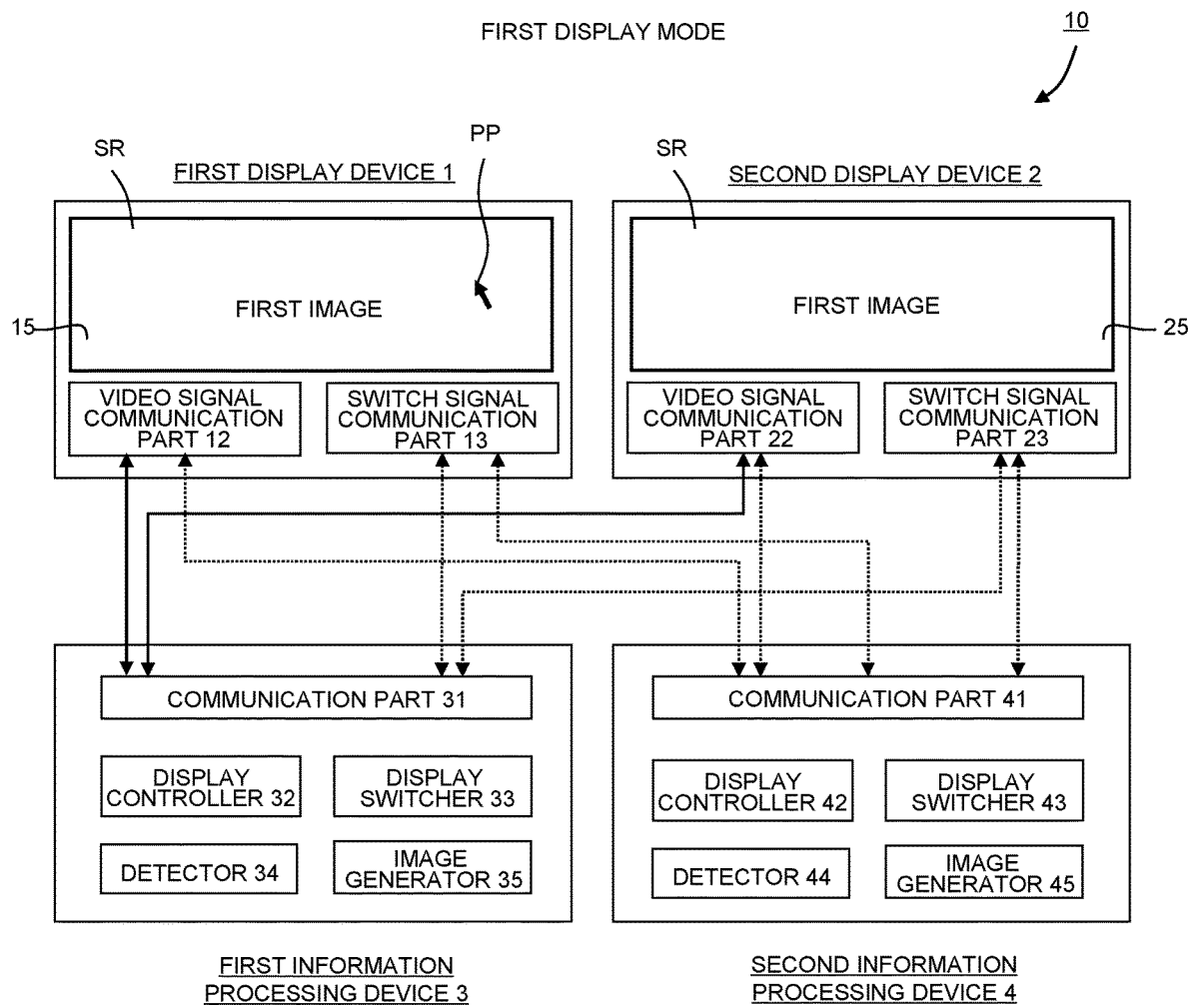
FIG. 3 is a schematic diagram showing a state in which a first image is displayed across the first and second display devices 1 and 2. That is, in the state of FIG. 3, the first and second display devices 1 and 2 perform extended display with respect to the first image.

In S1, the first and second display devices 1 and 2 included in the display system 10 perform the extended display with respect to the image (the first image) output from the first information processing device 3. This corresponds to the first display mode shown in FIG. 3. Here, in the present embodiment, when the image is displayed on the first and second display devices 1 and 2 in the extended display manner, the switch area SR is arranged in a direction perpendicular to a direction in which the first and second display devices 1 and 2 are arranged. The first and second display devices each include an end portion provided in a vertical direction corresponding to the direction perpendicular to the direction (horizontal direction) in which the first and second display devices are arranged. In the example of FIG. 3, the switch area SR is arranged in the end of the first display device 1 or the end of the second display device 2. The reason for the switch area SR arranged in the vertical direction is to suppress unnecessary switch processing when the pointing position on the first and second display devices 1 and 2 is moved with the operation device 5. The position, where the switch area SR is arranged, is not particularly limited, and the switch area SR may be arranged in an arbitrary area such as an end portion, which is provided in the horizontal direction, of the first display device 1 or the second display device 2. Further, the switch area SR is a virtual area, may be arranged on the first image or the second image, and may be highlighted when the pointing position PP overlaps on the switch area SR.

Figure 2:
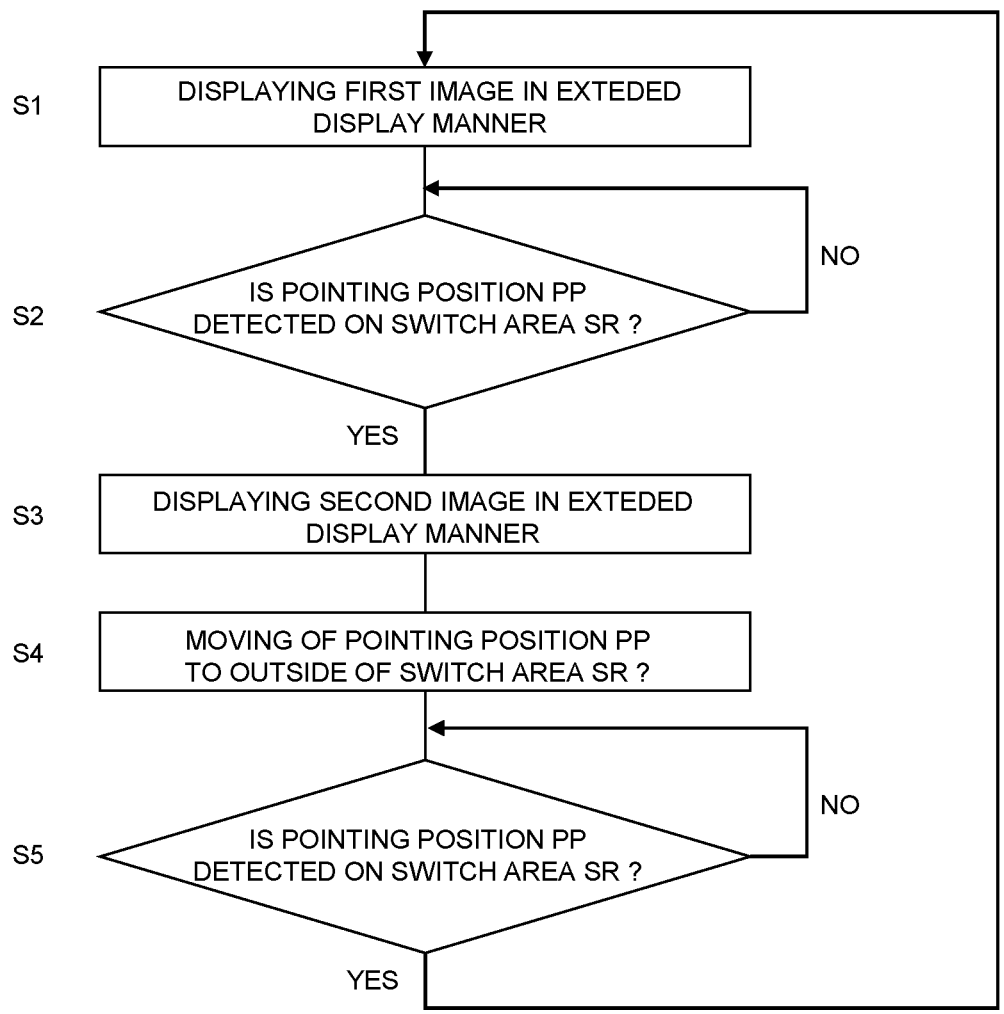
FIG. 2 is a flowchart showing processing of the display system 10 according to the first embodiment.
Figure 4:
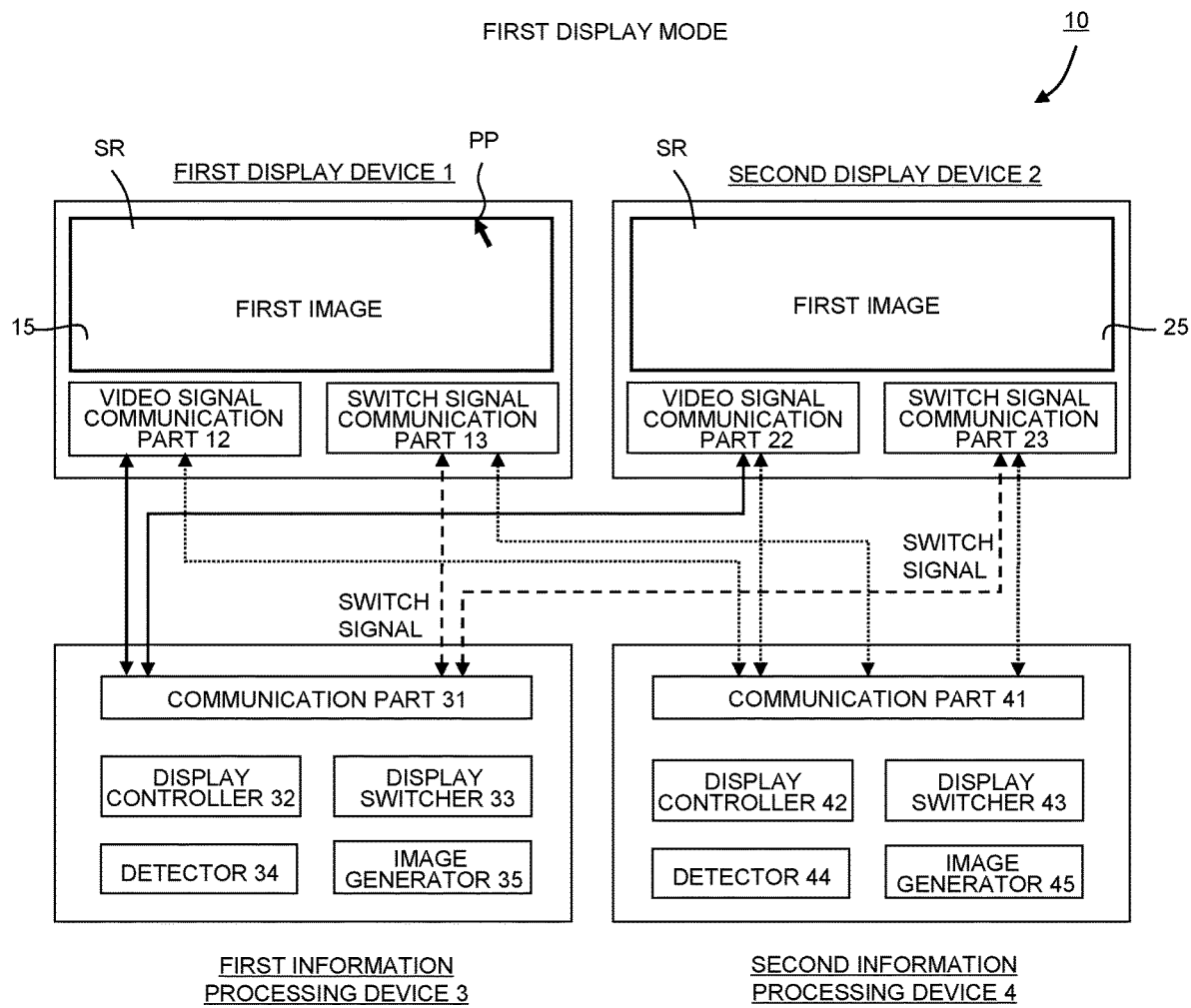
FIG. 4 is a schematic diagram showing a state in which a pointing position PP is positioned on the switch area SR.
Figure 5:
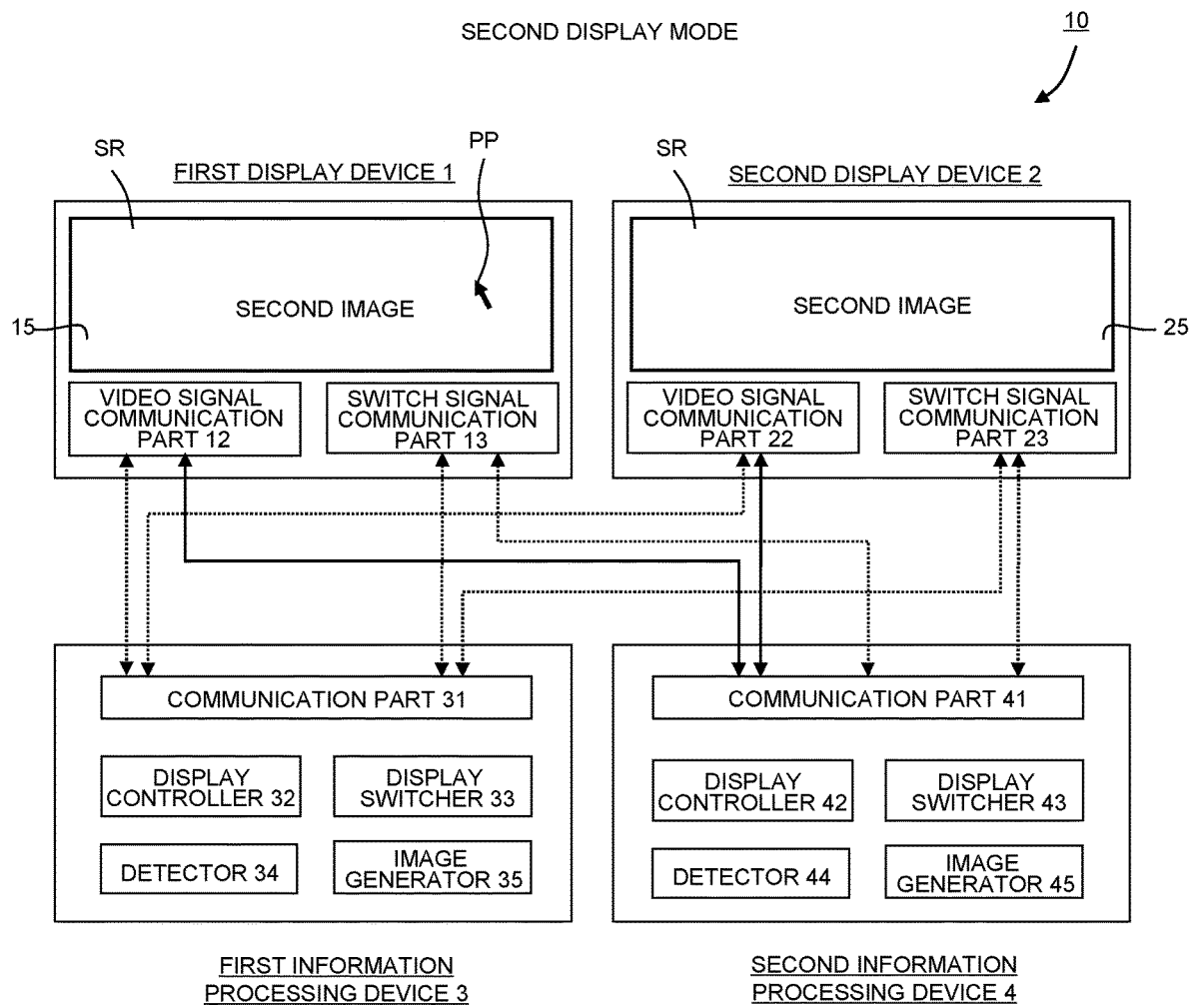
FIG. 5 is a schematic diagram showing a state in which a second image is displayed across the first and second display devices 1 and 2. That is, in the state of FIG. 5, the first and second display devices 1 and 2 perform extended display with respect to the second image.

Next, as shown in FIG. 4, when the operation device 5 is operated to move the pointing position PP into the switch area SR, in S2 of FIG. 2, the detector 34 detects that the pointing position PP is positioned on the switch area SR. Then, when the pointing position PP is detected by the detector 34, as shown in FIG. 4, the first information processing device 3 transfers the switch signal to the first and second display devices 1 and 2 to display the second image on the first and second display devices 1 and 2 in the extended display manner in S3 (the second display mode). Here, the switch signal is a signal for switching the image, displayed on the first and second display devices 1 and 2 in the extended display manner, from the first image to the second image. In other words, the switch signal is the signal for switching the display mode executed by the display system 10 from the first display mode to the second display mode. Thus, the display mode executed by the display system 10 is switched from the first display mode to the second display mode shown in FIG. 5. Note that FIG. 5 shows a state in which the pointing position PP moves outside the switch area SR in S4. Thus, the display system 10 continues to execute the second display mode. When the detector 34 does not detect the pointing position PP on the switch area SR, the processing waits until the detector 34 detects the pointing position PP on the switch area SR.

Figure 6:
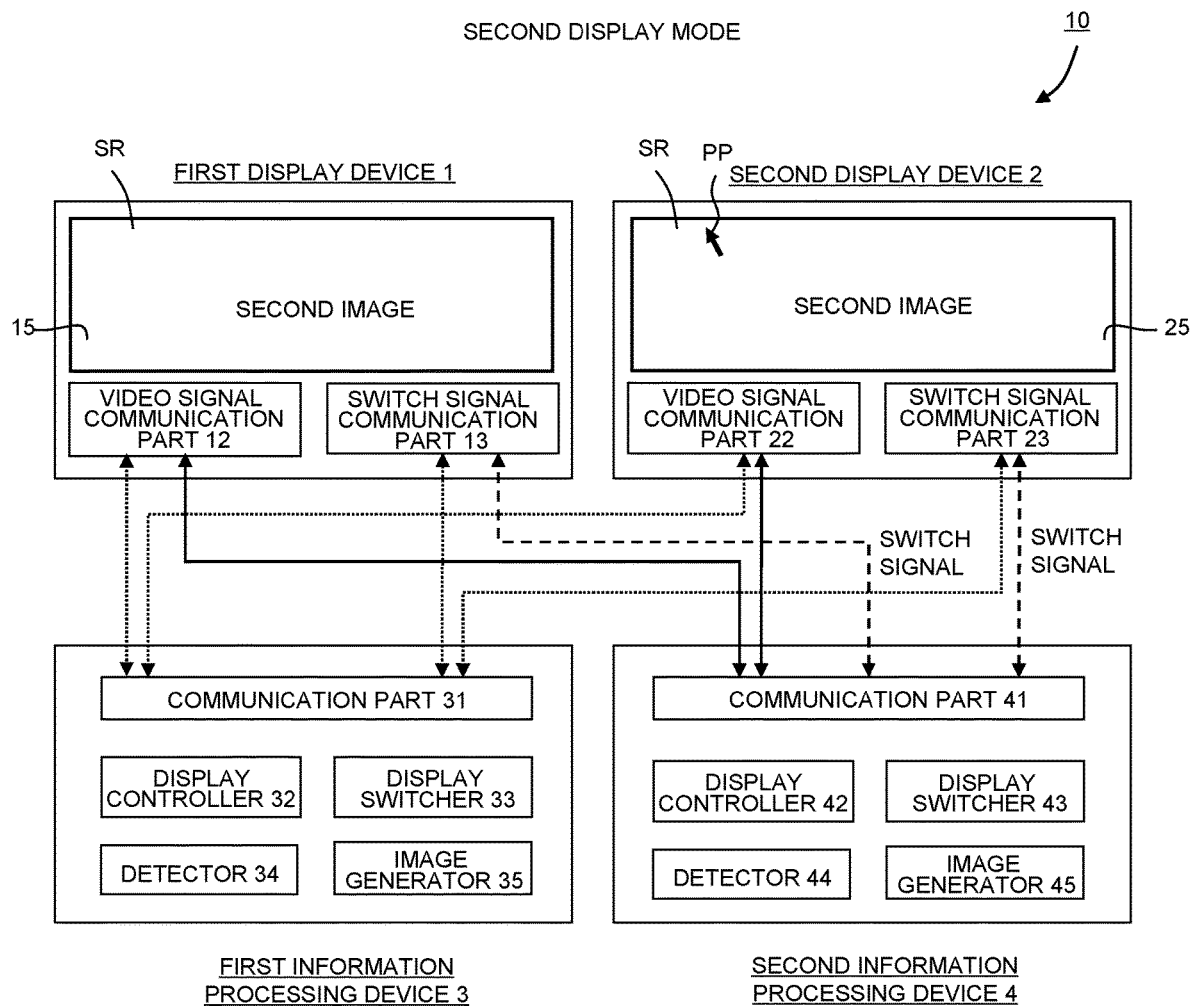
FIG. 6 is a schematic diagram showing a state in which a pointing position PP is positioned on the switch area SR.

Next, as shown in FIG. 6, when users operate the operation device 5 to move the pointing position PP into the switch area SR, in S5 of FIG. 2, the detector 44 detects the pointing position PP in the switch area SR. Then, when the detector 44 detects the pointing position PP, the processing returns to S1 again. Then, as shown in FIG. 6, the second information processing device 4 transfers the switch signal to the first and second display devices 1 and 2 to display the first image on the first and second display devices 1 and 2 in the extended display manner (first display mode). Thus, the display mode executed by the display system 10 is switched from the second display mode to the first display mode, and the state of the display system 10 returns to the state shown in FIG. 3. When the detector 44 does not detect the pointing position PP in the switch area SR, the processing waits until the detector 34 detects the pointing position PP in the switch area SR.

Here, regarding FIGS. 3 to 6, the display switcher 33 or the display switcher 43 may display information, indicating whether the image displayed on the first and second display devices 1 and 2 is the first image or the second image, on at least one of the first and second display devices 1 and 2. For example, after switching the display mode from the first display mode to the second display mode, the characters "second image" may be displayed on the entire screen of at least one of the first and second display devices 1 and 2 for a predetermined time. Conversely, after switching the display mode from the second display mode to the first display mode, the characters "first image" may be displayed on the entire screen of at least one of the first and second display devices 1 and 2 for a predetermined time. Further, the information related to at least one of the first and second display devices 1 and 2 may be displayed by a predetermined operation of the operation device 5. And the first display device 1 or the second display device 2 may be configured to display an electrical health record.

As described above, the display system 10 according to the first embodiment includes the display switcher 33 that switches the display mode from the first display mode to the second display mode when the detector 34 detects the pointing position PP in the first display mode. Thus, the display system 10 according to the first embodiment can easily switch the image, displayed across the first and second display devices 1 and 2, between the first image and the second image by moving the pointing position PP to the switch area SR.

2. Second Embodiment

Hereinafter, the display system 10 according to the second embodiment of the present invention will be described with reference to FIGS. 7 to 9. In the display system 10 according to the second embodiment, the switch area SR includes at least one of the first switch area SR1 arranged in the first display device 1 and the second switch area SR2 arranged in the second display device 2. Further, when the detector 34 (the detector 44) detects that the pointing position PP has been positioned on the first switch area SR1, the display switcher 33 (the display switcher 43) is configured to switch the display mode from the first display mode to the second display mode.

Figure 7:
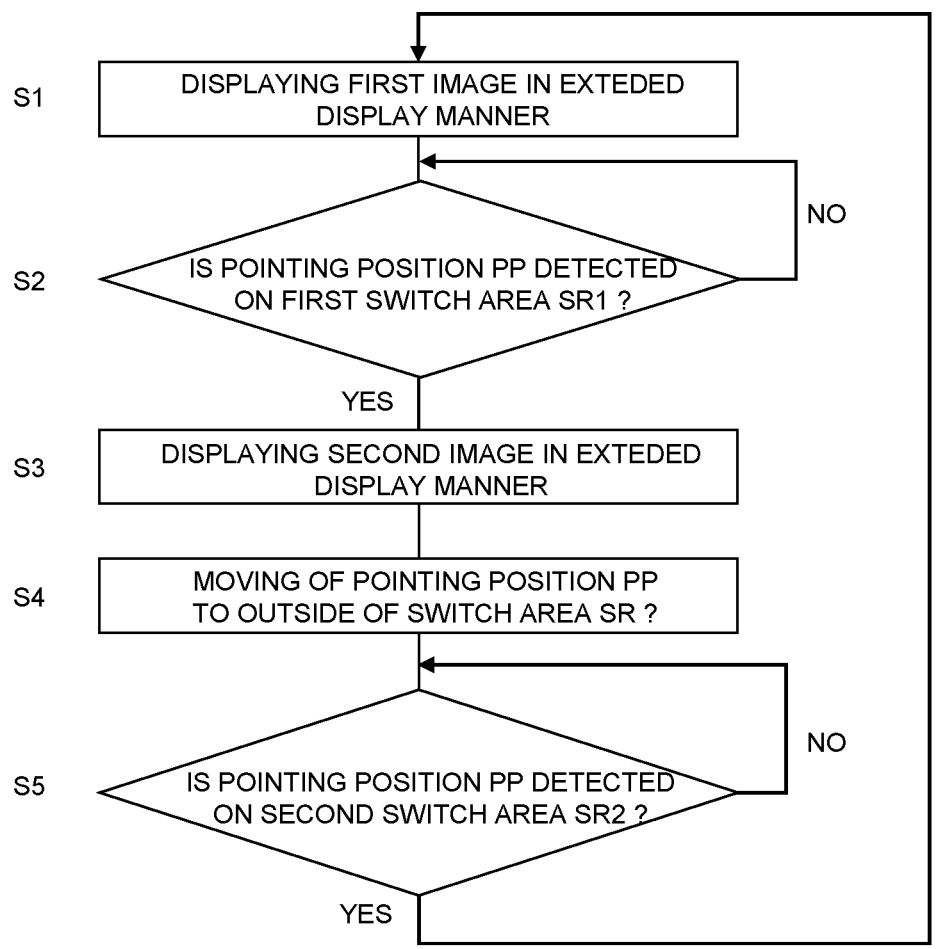
FIG. 7 is a flowchart showing processing of the display system 10 according to the second embodiment.

As shown in FIG. 7, in S1, the first and second display devices 1 and 2, included in the display system 10, perform extended display with respect to the image (the first image) output from the first information processing device 3. This corresponds to the first display mode in FIG. 8A.

Figure 8A:
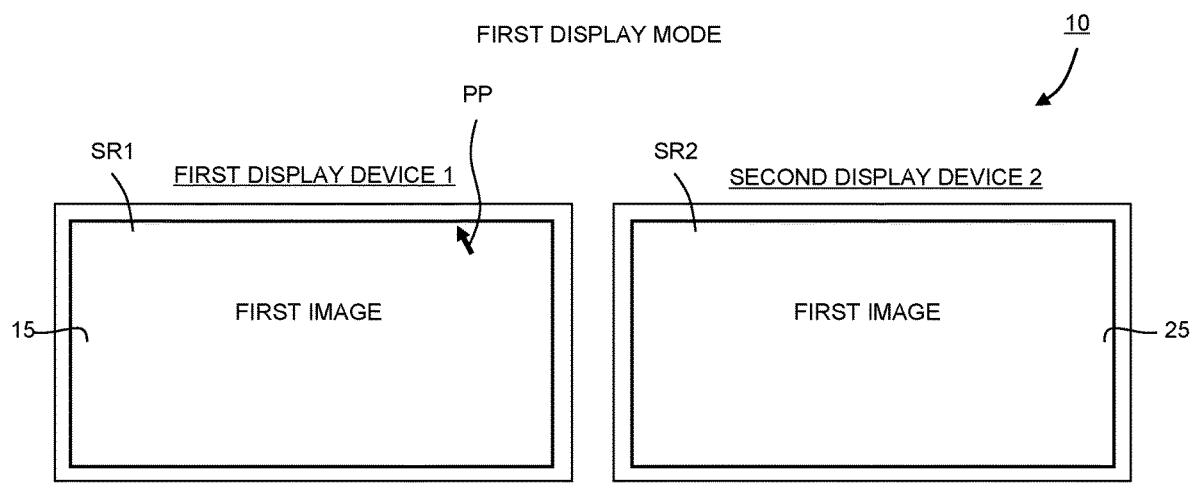
FIG. 8A is a schematic diagram showing a state in which the pointing position PP is positioned on a first switch area when the display system 10 of the second embodiment displays the first image across the first and second display devices 1 and 2.
Figure 8B:
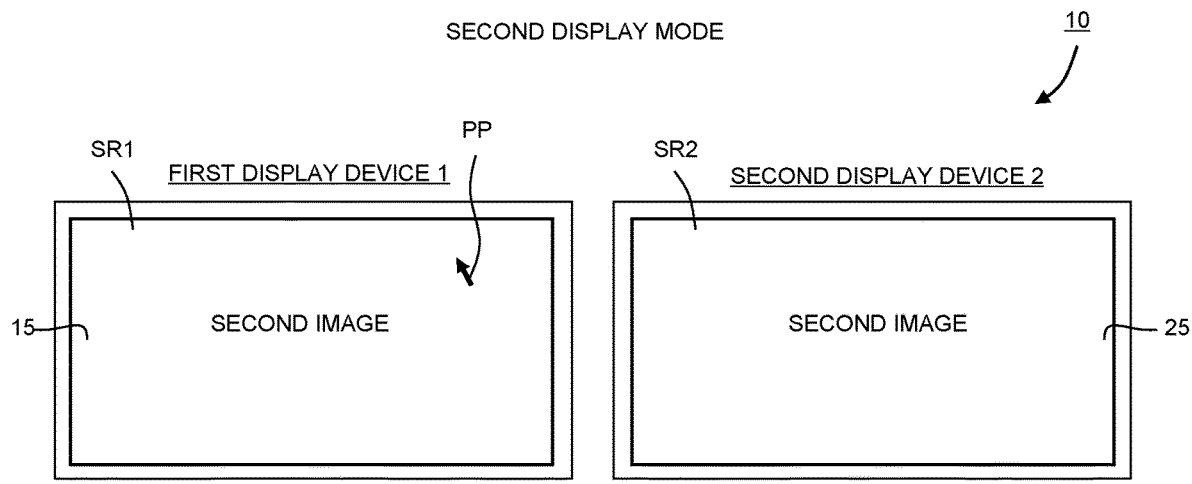
FIG. 8B is a schematic diagram showing a state in which a display switcher 33 has switched a display mode from a first display mode to a second display mode when the display system 10 of the second embodiment detects that the pointing position PP is positioned on the first switch area.

Next, as shown in FIG. 8A, when the users operate the operation device 5 to move the pointing position PP into the first switch area SR1, the detector 34 detects the pointing position PP in the first switch area SR1 in S2 of FIG. 7. Then, when the detector 34 detects the pointing position PP, the first information processing device 3 transfers the switch signal to the first and second display devices 1 and 2 to display the second image on the first and second display devices 1 and 2 in the extended display manner in S3 (the second display mode). Thus, the display mode executed by the display system 10 is switched from the first display mode to the second display mode, as shown in FIG. 8B. Note that FIG. 8B shows a state in which the pointing position PP moves outside the switch area SR in S4. Thus, the display system 10 continues to execute the second display mode. When the detector 34 does not detect the pointing position PP in the first switch area SR1, the processing waits until the detector 34 detects the pointing position PP in the first switch area SR1.

Figure 9A:
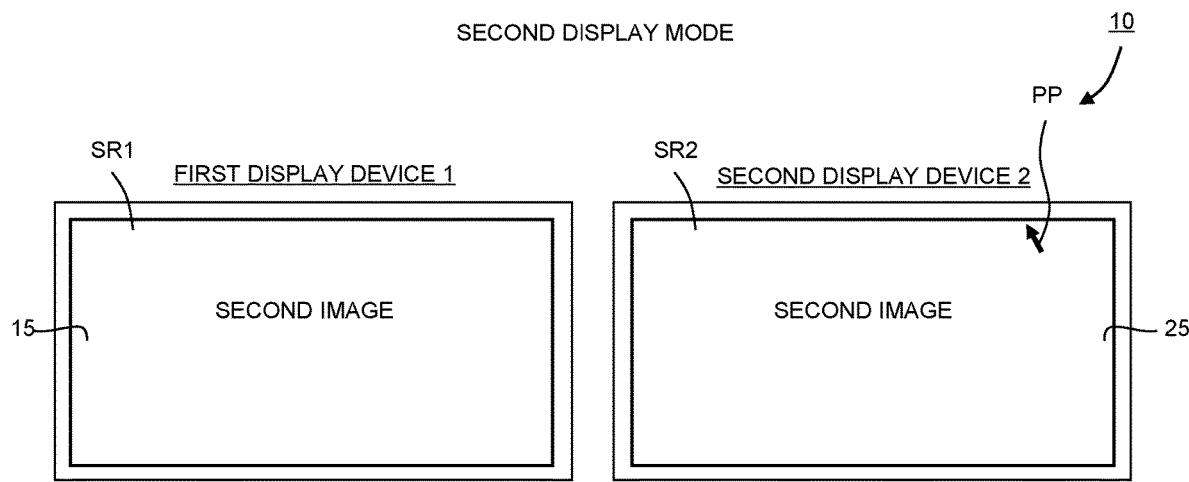
FIG. 9A is a schematic diagram showing a state in which the pointing position PP is positioned on a second switch area when the display system 10 of the second embodiment displays the second image across the first and second display devices 1 and 2.
Figure 9B:
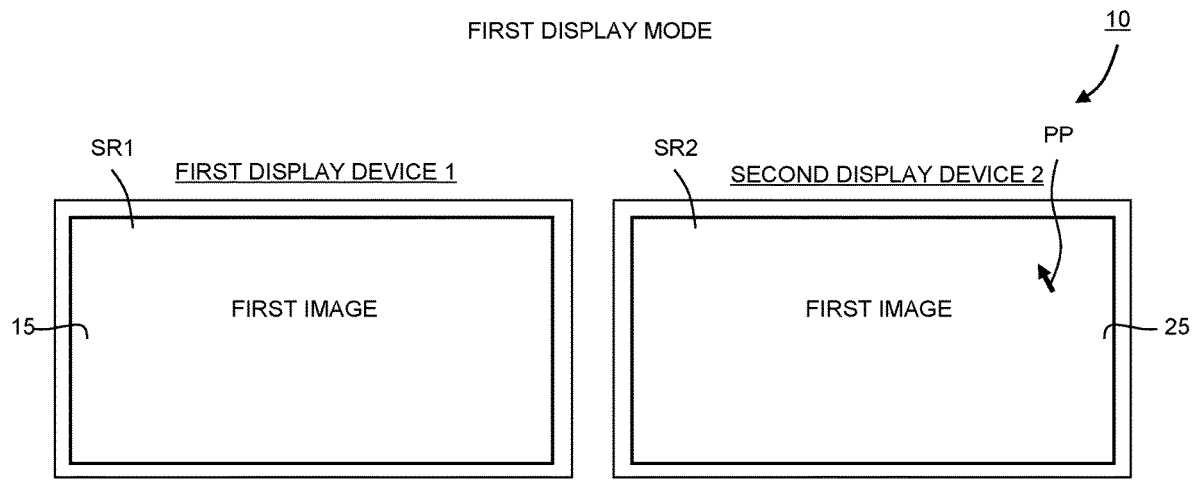
FIG. 9B is a schematic diagram showing a state in which a display switcher 43 has switched the display mode from the second display mode to the first display mode when the display system 10 of the second embodiment detects that the pointing position PP is positioned on the second switch area.

Next, as shown in FIG. 9A, when the users operate the operation device 5 to move the pointing position PP into the second switch area SR2, in S5 of FIG. 7, the detector 44 detects the pointing position PP in the second switch area SR2. Then, when the detector 44 detects the pointing position PP, the processing returns to S1 again. The second information processing device 4 transfers the switch signal to the first and second display devices 1 and 2 to display the first image on the first and second display devices 1 and 2 in the extended display manner (the first display mode). Thus, the display mode executed by the display system 10 is switched from the second display mode to the first display mode, and the state of the display system 10 turns to the state shown in FIG. 9B. When the detector 44 does not detect the pointing position PP in the second switch area SR2, the processing waits until the detector 34 detects the pointing position PP in the second switch area SR2.

As described above, the display system 10 according to the second embodiment switches, when the pointing position PP has been positioned on the first switch area SR1 while the first and second display devices 1 and 2 displays the first image in the extended display manner (first display mode), the display mode from the first display mode to the second display mode. And the display system 10 switches, when the pointing position PP has been positioned on the second switch area SR2 while the first and second display devices 1 and 2 displays the second image in the extended display manner (second display mode), the display mode from the second display mode to the first display mode.

In other words, when the image displayed on the first and second display devices 1 and 2 in the extended display manner is the first image, only the first switch area SR1, which is provided in the first display device 1 located near the first information processing device 3 that generates the first image, is active with respect to the pointing position PP. When the image displayed on the first and second display devices 1 and 2 in the extended display manner is the second image, only the second switch area SR2, which is provided in the second display device 2 located near the second information processing device 4 that generates the second image, is active with respect to the pointing position PP. Thus, the display system 10 can control the display mode so that the switching of the display mode from the first display mode to the second display mode is not executed when the pointing position PP has been positioned on the second switch area SR2 in the first display mode. And the display system 10 can control the display mode so that the switching of the display mode from the second display mode to the first display mode is not executed when the pointing position PP has been positioned on the first switch area SR1 in the second display mode.

Thus, the users can intuitively understand whether the image, displayed on the first and second display devices 1 and 2 in the extended display manner, is the first image (first display mode) or the second image (second display mode) without displaying the information, indicating whether the image displayed on the first and second display devices 1 and 2 in the extended display manner is the first image or the second image, on the at least one of first and second display devices 1 and 2.

3. Third Embodiment

Hereinafter, the display system 10 according to the third embodiment of the present invention will be described with reference to FIGS. 10 to 12. In the display system 10 according to the third embodiment, the switch area SR includes at least one of the first switch area SR1 arranged in the first display device 1 and the second switch area SR2 arranged in the second display device 2. Further, when the detector 44 (detector 34) detects that the pointing position PP is positioned on the first switch area SR1, the display switcher 43 (display switcher 33) is configured to switch the display mode from the second display mode to the first display mode.

Figure 10:
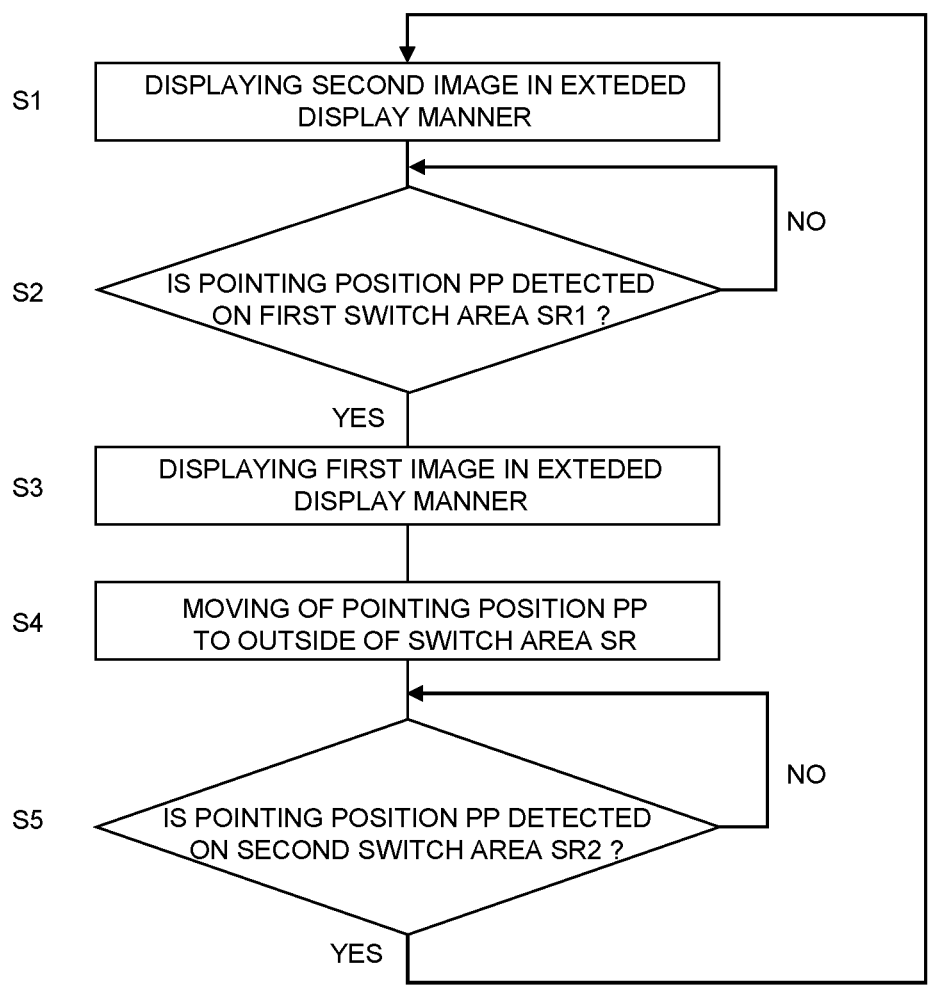
FIG. 10 is a flowchart showing processing of the display system 10 according to the third embodiment.

As shown in FIG. 10, in S1, the first and second display devices 1 and 2 included in the display system 10 perform extended display with respect to the image (the second image) output from the second information processing device 4. This corresponds to the second display mode shown in FIG. 11A.

Figure 11A:
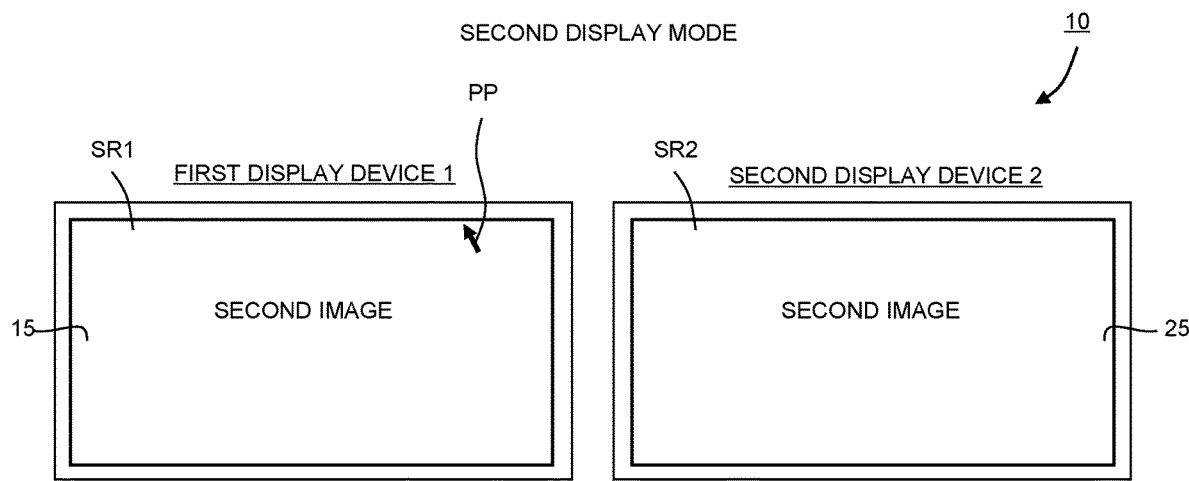
FIG. 11A is a schematic diagram showing a state in which the pointing position PP is positioned on the first switch area when the display system 10 of the third embodiment displays the second image across the first and second display devices 1 and 2.
Figure 11B:
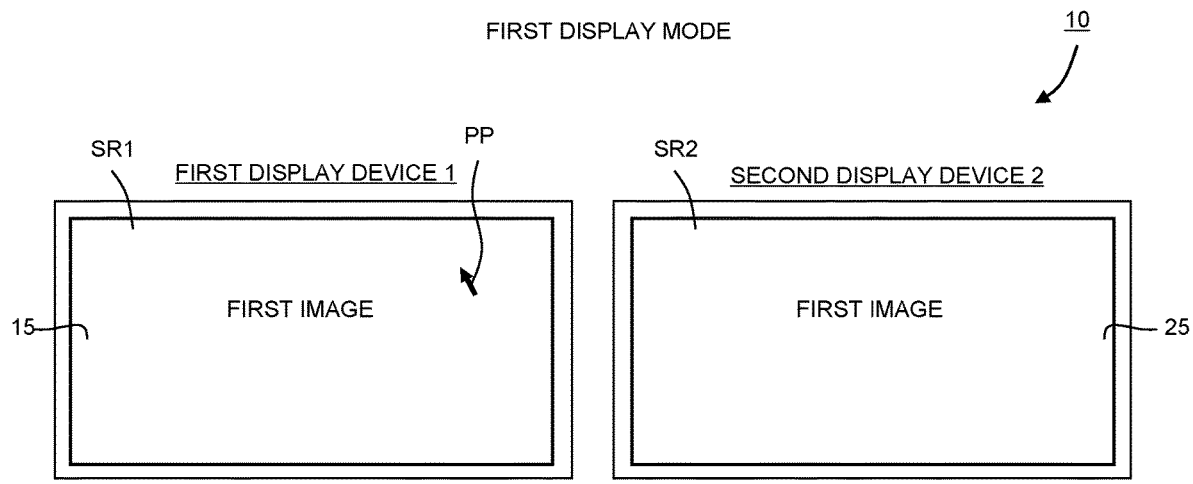
FIG. 11B is a schematic diagram showing a state in which the display switcher 43 has switched the display mode from the second display mode to the first display mode when the display system 10 of the third embodiment detects that the pointing position PP is positioned on the first switch area.

Next, as shown in FIG. 11A, when the users operate the operation device 5 to move the pointing position PP into the first switch area SR1, the detector 44 detects the pointing position PP in the first switch area SR1 in S2 of FIG. 10. Then, when the detector 44 detects the pointing position PP, the second information processing device 4 transfers the switch signal to the first and second display devices 1 and 2 to display the first image on the first and second display devices 1 and 2 in the extended display manner in S3 (the first display mode). Thus, the display mode executed by the display system 10 is switched from the second display mode to the first display mode, as shown in FIG. 11B. Note that FIG. 11B shows a state in which the pointing position PP moves outside the switch area SR in S4. Thus, the display system 10 continues to execute the first display mode, and the state of display system 10 turns to the state in FIG. 11B. When the detector 44 does not detect the pointing position PP in the first switch area SR1, the processing waits until the detector 44 detects the pointing position PP in the first switch area SR1.

Figure 12A:
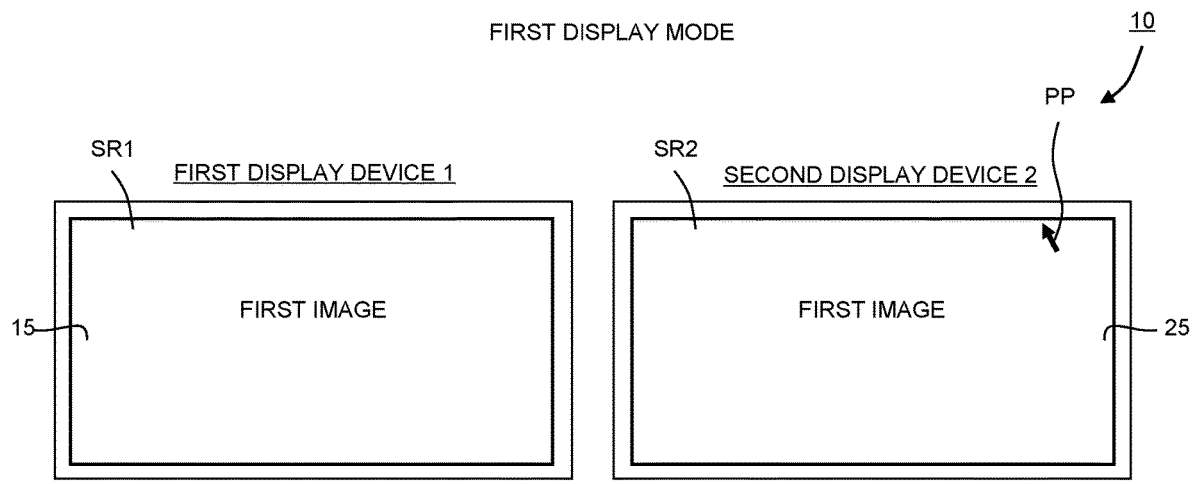
FIG. 12A is a schematic diagram showing a state in which the pointing position PP is positioned on the second switch area when the display system 10 of the third embodiment displays the first image across the first and second display devices 1 and 2.
Figure 12B:
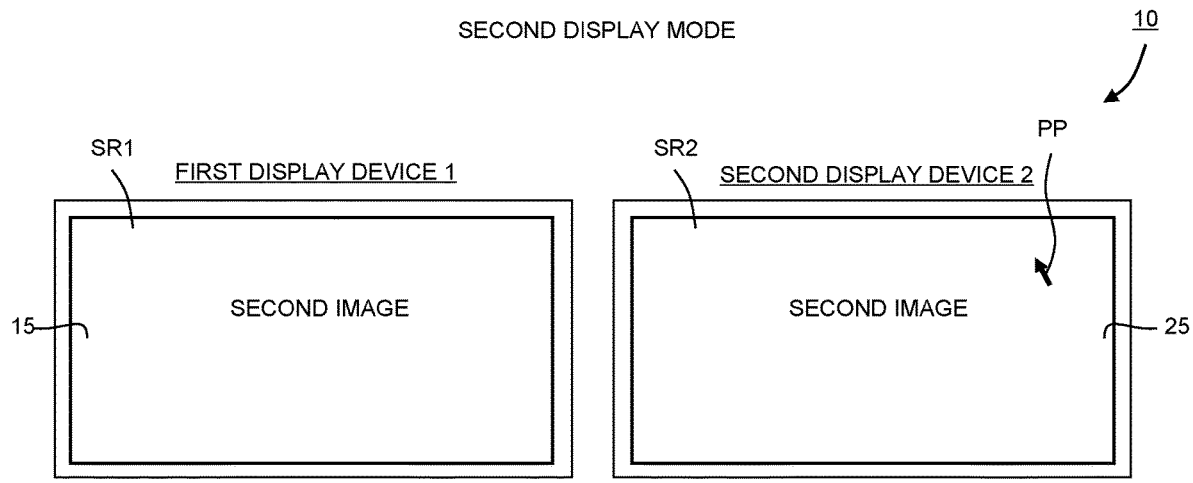
FIG. 12B is a schematic diagram showing a state in which the display switcher 33 has switched the display mode from the first display mode to the second display mode when the display system 10 of the third embodiment detects that the pointing position PP is positioned on the second switch area.

Next, as shown in FIG. 12A, when the users operate the operation device 5 to move the pointing position PP into the second switch area SR2, the detector 34 detects the pointing position PP in the second switch area SR2 in S4 of FIG. 10. Then, when the detector 34 detects the pointing position PP, the processing returns to S1 again, and the first information processing device 3 transfers the switch signal to the first and second display devices 1 and 2 to display the second image on the first and second display devices 1 and 2 in the extended display manner (the second display mode). Thus, the display mode executed by the display system 10 is switched from the first display mode to the second display mode, and the state of the display system 10 turns to the state shown in FIG. 12B. When the detector 34 does not detect the pointing position PP in the second switch area SR2, the processing waits until the detector 34 detects the pointing position PP in the second switch area SR2.

As described above, the display system 10 according to the third embodiment switches, when the pointing position PP is positioned on the first switch area SR1 while the first and second display devices 1 and 2 displays the second image in the extended display manner (the second display mode), the display mode from the second display mode to the first display mode. And the display system 10 switches, when the pointing position PP is positioned on the second switch area SR2 while the first and second display devices 1 and 2 displays the first image in the extended display manner (first display mode), the display mode from the first display mode to the second display mode.

In other words, in the case that the image displayed on the first and second display devices 1 and 2 in the extended display manner is the second image, when the pointing position PP has been positioned on the first switch area SRL which is provided in the first display device 1 located near the first information processing device 3 that generates the first image, the display system 10 can display the first image (the first display mode). And in the case that the image displayed on the first and second display devices 1 and 2 in the extended display manner is the first image, when the pointing position PP has been positioned on the second switch area SR2, which is provided in the second display device 2 located near the second information processing device 4 that generates the second image, the display system 10 can display the second image (the second display mode). Thus, the display system 10 can control the display mode so that the switching of the display mode from the second display mode to the first display mode is executed when the pointing position PP has been positioned on the first switch area SR1 in the second display mode. And the display system 10 can control the display mode so that the switching of the display mode from the first display mode to the second display mode is executed when the pointing position PP has been positioned on the second switch area SR2 in the first display mode.

Thus, the users can intuitively understand whether the image, displayed on the first and second display devices 1 and 2 in the extended display manner, is the first image (first display mode) or the second image (second display mode) without displaying the information, indicating whether the image displayed on the first and second display devices 1 and 2 in the extended display manner is the first image or the second image, on the at least one of first and second display devices 1 and 2.

4. Fourth Embodiment

4-1. Display System 10

Figure 13:
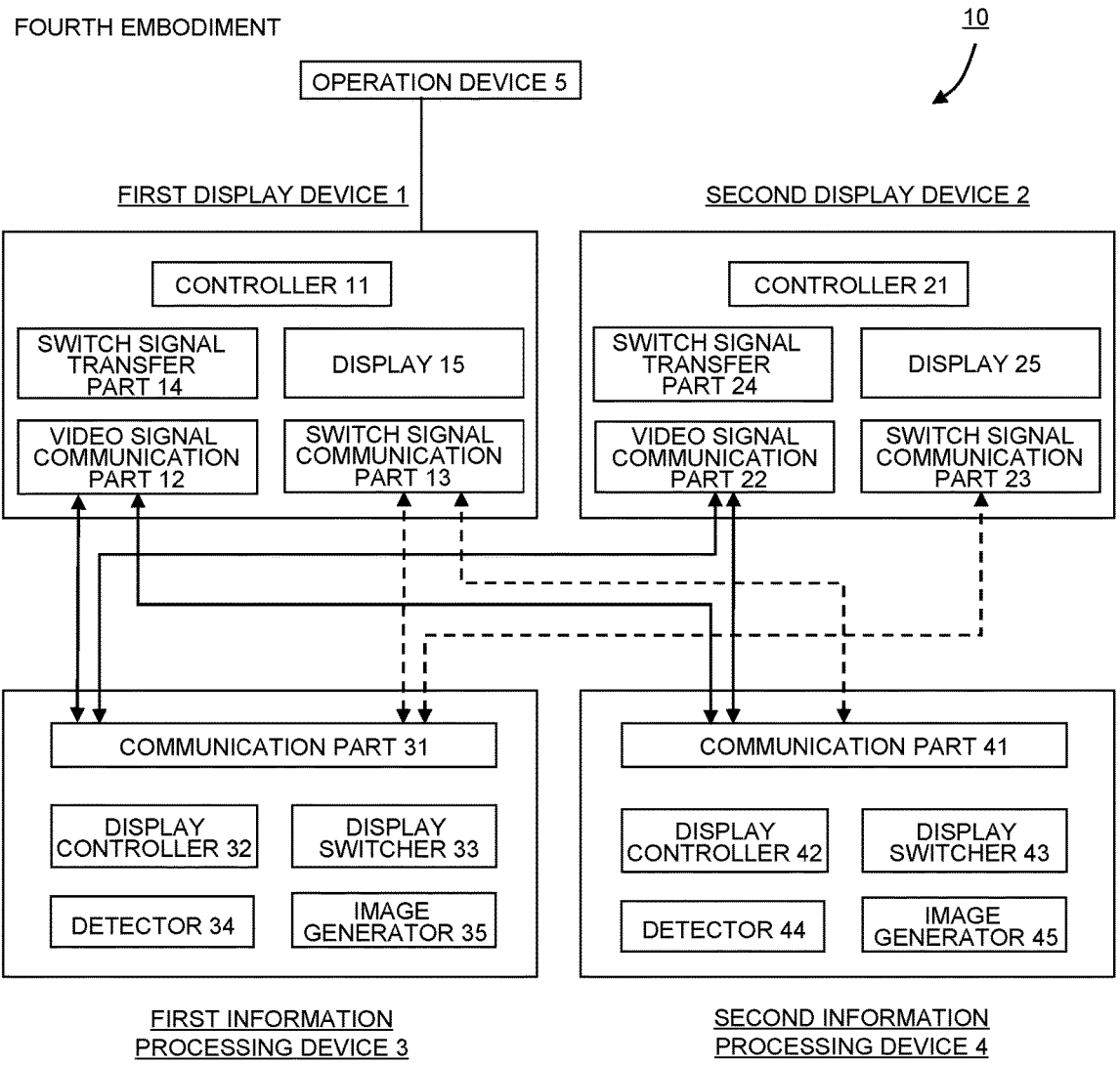
FIG. 13 is a functional block diagram showing the configuration of the display system 10 according to the fourth embodiment of the present invention.
Figure 14:
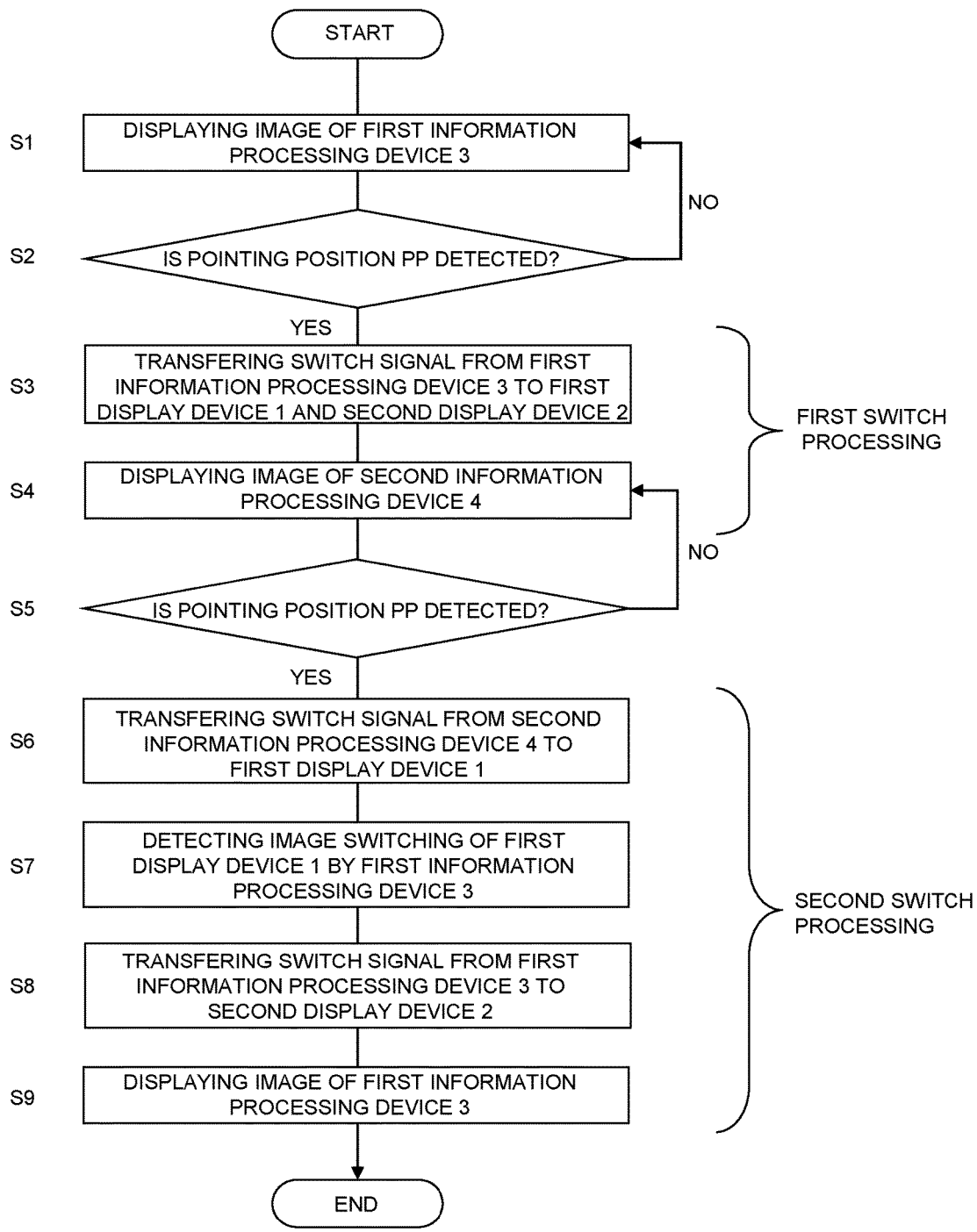
FIG. 14 is a flowchart showing processing of the display system 10 according to the fourth embodiment.

Hereinafter, the display system 10 according to the fourth embodiment of the present invention will be described with reference to FIGS. 13 and 14. FIG. 13 is a functional block diagram of the display system 10 according to the fourth embodiment of the present invention. In the fourth embodiment, the first display device 1 includes a switch signal transfer part 14, and the second display device 2 includes a switch signal transfer part 24. When the switch signal transfer part 14 transfers the switch signal, input from the second information processing device 4, to the first information processing device 3, or when the switch signal is input from the second information processing device 4 to the switch signal transfer part 14, the switch signal transfer part 14 outputs a signal, indicating that the switch signal is input, to the first information processing device 3. When the switch signal transfer part 14 transfers the switch signal, input from the first information processing device 3, to the second information processing device 4, or when the switch signal is input from the first information processing device 3 to the switch signal transfer part 24, the switch signal transfer part 24 outputs a signal, indicating that the switch signal is input, to the second information processing device 4.

In the present embodiment, the switch signal communication part 23 of the second display device 2 is configured to communicate with the communication part 31 of the first information processing device 3, but cannot communicate with the communication part 41 of the second information processing device 4. The present embodiment assumes a case where the switch signal communication part 23 is a USB port, the second display device 2 has only one USB port, and the second display device 2 can be connected to only one information processing device.

4-2. Flowchart of Fourth Embodiment

Next, the processing executed by the display system 10 will be described with reference to FIG. 14.

In S1, the first and second display devices 1 and 2 included in the display system 10 perform the extended display (the first display mode) with respect to the image (the first image) output from the first information processing device 3.

Next, when the operation device 5 is operated to move the pointing position PP into the switch area SR, the detector 34 detects that the pointing position PP is positioned on the switch area SR in S2. Then, when the pointing position PP is detected by the detector 34, the display system 10 starts to execute the first switch processing. When the detector 34 does not detect the presence of the pointing position PP on the switch area SR, the processing returns to S1.

Next, in S3, the switch signal is transmitted from first information processing device 3 to the first and second display devices 1 and 2. Here, this switch signal is a signal for switching the image, displayed on the first display device 1 or the second display device 2, to the second image. Specifically this switch signal is an instruction signal for establishing communication with the communication part 41 of the second information processing device 4 and the first and second display devices 1 and 2.

Then, in S4, when the first and second display devices 1 and 2 receive the switch signal, the first and second display devices 1 and 2 display the second image output from the second information processing device 4 in the extended display manner (the second display mode).

Thus, the processing in S3 and S4 is the first switch processing. That is, the first switching processing is a switch processing that switches the image, displayed on the first and second display devices 1 and 2 in the extended display manner, from the image of the first information processing device 3 to the image of the second information processing device 4. In the first switch processing of the present embodiment, the first switch processing is executed by outputting the switch signal from the first information processing device 3 to the first and second display devices 1 and 2.

Next, when the operation device 5 is operated to move the pointing position PP into the switch area SR, the detector 44 detects that the pointing position PP is positioned on the switch area SR in S5. Then, when the pointing position PP is detected by the detector 44, the display system 10 starts to execute the second switch processing. When the detector 44 does not detect the presence of the pointing position PP on the switch area SR, the processing returns to S4.

Next, in S6, the switch signal is transmitted from the second information processing device 4 to the first display device 1. Here, this switch signal is a signal for switching the image, displayed on the first display device 1, to the first image. Then, the communication part 41 of the second information processing device 4 and the switch signal communication part 23 of the second display device 2 are not connected, so the second information processing device 4 cannot send the switch signal to the second display device 2. Thus, the first image is displayed on the first display device 1, and the second image is displayed on the second display device 2.

Next, in S7, the first information processing device 3 detects the switching of the image of the first display device 1. In the present embodiment, the first information processing device 3 detects, via the video signal communication part 12 of the first display device 1, whether the image displayed on the first display device 1 has been switched.

Next, in S8, the switch signal is transmitted from the first information processing device 3 to the second display device 2. Here, this switch signal is a signal for switching the image, displayed on the second display device 2, to the first image. As described above, in this embodiment, when the image displayed on the first display device 1 has been switched, the first information processing device 3 outputs the switch signal to the second display device 2 so that the second display device 2 displays the image (the first image) output from the first information processing device 3.

Here, instead of the processing in S7, the first information processing device 3 may detect that the signal has been output from the second information processing device 4 by using the switch signal transfer part 14 of the first display device 1. Specifically, the switch signal transfer part 14 of the first display device 1 transfers the switch signal, input from the second information processing device 4, to the first information processing device 3. Or, when the switch signal is input from the second information processing device 4, the switch signal transfer part 14 of the first display device 1 outputs a signal, indicating that the switch signal has been input, to the first information processing device 3. And the first information processing device 3 may be configured to, when the first information processing device 3 receives the signal output from the switch signal transfer part 14, output the switch signal to the second display device 2.

Then, in S9, when the second display device 2 receives the switch signal, the second display device 2 displays the image (the first image) of the first information processing device 3. Thus, the display mode switches to the first display mode again. In this way, the processing from S6 to S9 is the second switch processing. That is, the second switch processing is a switch processing that switches the image, displayed on the first and second display devices 1 and 2 in the extended display manner, from the image of the second information processing device 4 to the first information processing device 3. In the present embodiment, the second switch processing is executed by outputting the switch signal from the first information processing device 3 to the second display device 2 after the second information processing device 4 outputs the switch signal to the first display device 1 and the first display device 1 receives the switch signal from the second information processing device 4.

As described above, in the display system 10 according to the fourth embodiment, the second information processing device 4 is configured to output the switch signal for switching the image displayed on the first display device 1 to the first display device 1. Then, the first information processing device 3 is configured to output the switch signal for switching the image displayed on the second display device 2 to the second display device 2 according to the switch signal. Thus, even if the switch signal communication part 23 of the second display device 2 and the communication part 41 of the second information processing device 4 cannot communicate the switch signal with one another, the display system 10 can control a plurality of the display devices.

As described above, the display system 10 according to the fourth embodiment can control the plurality of the display devices even in the case that the switch signal communication part 13 of the first display device 1 and the switch signal communication part 23 of the second display device 2 each has only one port and can communicate with only one of the first information processing device 3 and the second information processing device 4.

4. Another Embodiment

Although various embodiments have been described above, the present invention is not limited to these.

For example, each component of the first information processing device 3 or the second information processing device 4 may be incorporated when the first information processing device 3 or the second information processing device 4 is manufactured. Or, each component of the first information processing device 3 or the second information processing device 4 may be realized by an application downloaded via the Internet after the shipment of the first information processing device 3 or the second information processing device 4.

The embodiment according to the present invention is also realized with following configurations.

A program causing a computer to function as a controller that controls a display system including first and second information processing devices and first and second display devices, the first and second display devices being configured to switch between
a first display mode, in which a first image output from the first information processing device is displayed across the first and second display devices, and
a second display mode, in which a second image output from the second information processing device is displayed across the first and second display devices, the program comprising:
detecting, by a detector, whether a pointing position is positioned on a switch area arranged in at least one of the first and second display devices; and
switching, by a display switcher, a display mode from the first display mode to the second display mode when the detector detects the pointing position on the switch area in the first display mode.

Further, the embodiment of the present invention is also realized with a configuration that the above program is stored in a non-transitory computer-readable medium.

DESCRIPTION OF REFERENCE SIGNS

1 first display device
2 second display device
3 first information processing device
4: second information processing device
5 operation device
10 display system
11 controller
12 video signal communication part
13 switch signal communication part
14 switch signal transfer part
15 display
21 controller
22 video signal communication part
23 switch signal communication part
24 switch signal transfer part
25 display
31 communication part
32 display controller
33 display switcher
34 detector
35 image generator
41 communication part
42 display controller
43 display switcher
44 detector
45 image generator
PP pointing position
SR switch area
SR1 first switch area
SR2 second switch area

The invention claimed is:
1. A display system comprising:
first and second information processing devices;
first and second display devices configured to switch between
a first display mode, in which a first image output from the first information processing device is displayed across the first and second display devices, and
a second display mode, in which a second image output from the second information processing device is displayed across the first and second display devices;
a detector configured to detect whether a pointing position is positioned on a switch area arranged in at least one of the first and second display devices; and
a display switcher configured to, when the detector detects the pointing position on the switch area in the first display mode, switch a display mode from the first display mode to the second display mode, wherein
the first and second display devices each includes a display, and the displays of the first and second display devices each includes an upper end portion, a lower end portion, a right end portion, and a left end portion and
the switch area includes first and second switch areas,
the first switch area is arranged in the upper end portion or the lower end portion of the display of the first display device, the first switch area extends from the right end portion to the left end portion of the display of the first display device, the second switch area is arranged in the upper end portion or the lower end portion of the display of the second display device, the second switch area extends from the right end portion to the left end portion of the display of the second display device.

2. A display system comprising:

first and second information processing devices;

first and second display devices configured to switch between a first display mode, in which a first image output from the first information processing device is displayed across the first and second display devices, and a second display mode, in which a second image output from the second information processing device is displayed across the first and second display devices;

a detector configured to detect whether a pointing position is positioned on a switch area arranged in at least one of the first and second display devices; and a display switcher configured to, when the detector detects the pointing position on the switch area in the first display mode, switch a display mode from the first display mode to the second display mode, when the detector detects the pointing position on the switch area in the second display mode, switches the display mode from the second display mode to the first display mode, wherein the first and second display devices each includes a display, and the displays of the first and second display devices each includes an upper end portion and a lower end portion, and the switch area is arranged in the upper end portion or the lower end portion of the display of the first display device or the display of the second display device.

3. The display system of claim 2, wherein the display switcher displays information, indicating whether an image displayed on the first and second display devices is the first image or the second image, on at least one of the first and second display devices.

4. The display system of claim 2, wherein the first display device or the second display device is configured to display an electrical health record.

5. A non-transitory computer readable medium that stores a program causing a computer to function as a controller that controls a display system including first and second information processing devices and first and second display devices, the first and second display devices being configured to switch between a first display mode, in which a first image output from the first information processing device is displayed across the first and second display devices, and a second display mode, in which a second image output from the second information processing device is displayed across the first and second display devices, the program comprising:

detecting, by a detector, whether a pointing position is positioned on a switch area arranged in at least one of the first and second display devices;

switching, by a display switcher, a display mode from the first display mode to the second display mode when the detector detects the pointing position on the switch area in the first display mode; and switching, by a display switcher, the display mode from the second display mode to the first display mode when the detector detects the pointing position on the switch area in the second display mode, wherein the first and second display devices each includes a display, and the displays of the first and second display devices each includes an upper end portion and a lower end portion, and the switch area is arranged in the upper end portion or the lower end portion of the display of the first display device or the display of the second display device.

* * * * *